United States Patent [19]

Simpson et al.

[11] 4,055,649
[45] Oct. 25, 1977

[54] 4-ALKYL-2,6-DI-(SECONDARY OR TERTIARY ALKYL)AMINO-3-FORMYLPYRIDINES PHARMACEUTICAL COMPOSITIONS THEREOF AND THEIR USE IN THE TREATMENT OF OBESITY AND DIABETES

[75] Inventors: William R. Simpson, Mendham; Robert J. Strohschein, Parsippany, both of N.J.

[73] Assignee: Sandoz, Inc., E. Hanover, N.J.

[21] Appl. No.: 655,428

[22] Filed: Feb. 5, 1976

[51] Int. Cl.$^2$ .................... A61K 31/44; C07D 213/74
[52] U.S. Cl. ................................ 424/263; 260/296 R; 260/563 R
[58] Field of Search ...................... 424/263; 260/296 R

[56] References Cited

U.S. PATENT DOCUMENTS

| 3,853,895 | 12/1974 | Lamm et al. ...................... 260/294.9 |
| 3,899,478 | 8/1975 | Fleckenstein ...................... 260/256 |
| 3,907,769 | 9/1975 | Dehnert et al. .................. 260/296 R |
| 3,947,463 | 3/1976 | Fleckenstein et al. ........ 260/294.8 G |
| 3,980,659 | 9/1976 | Fleckenstein et al. ........ 260/294.8 G |

FOREIGN PATENT DOCUMENTS

| 2,230,392 | 6/1972 | Germany |
| 1,377,506 | 12/1974 | United Kingdom |
| 1,420,411 | 1/1976 | United Kingdom |

OTHER PUBLICATIONS

Bernstein et al., J. Am. Chem. Soc., 69, 1151–1158, (1947).

*Primary Examiner*—Norman A. Drezin
*Attorney, Agent, or Firm*—Gerald D. Sharkin; Richard E. Vila; Melvyn M. Kassenoff

[57] ABSTRACT

Compounds of the formula

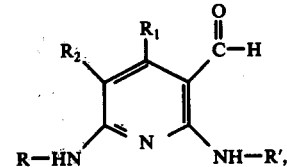

wherein
R is secondary alkyl of 3 to 7 carbon atoms or tertiary alkyl of 4 to 7 carbon atoms,
R' is secondary alkyl of 3 to 7 carbon atoms or tertiary alkyl of 4 to 7 carbon atoms,
$R_1$ is primary or secondary alkyl of 1 to 5 carbon atoms, and
$R_2$ is hydrogen, chloro or bromo, and the pharmaceutically acceptable acid addition salts thereof, are useful as anti-obesity and anti-diabetic agents. The compounds wherein R and R' are tertiary alkyl of 4 to 7 carbon atoms and $R_2$ is hydrogen are synthesized from ketenimines and amidines, all of the compounds wherein $R_2$ is hydrogen are synthesized by reduction of the corresponding 3-cyanopyridines, and the compounds wherein $R_2$ is chloro or bromo are synthesized from the corresponding compounds wherein $R_2$ is hydrogen and an N-halosuccinimide.

18 Claims, No Drawings

4-ALKYL-2,6-DI-(SECONDARY OR TERTIARY ALKYL)AMINO-3-FORMYLPYRIDINES PHARMACEUTICAL COMPOSITIONS THEREOF AND THEIR USE IN THE TREATMENT OF OBESITY AND DIABETES

This invention relates to compounds of the formula

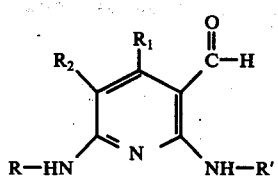

wherein
R is secondary alkyl of 3 to 7 arbon atoms or tertiary alkyl of 4 to 7 carbon atoms,
R' is secondary alkyl of 3 to 7 carbon atoms or tertiary alkyl of 4 to 7 carbon atoms,
$R_1$ is primary or secondary alkyl of 1 to 5 carbon atoms, and
$R_2$ is hydrogen, chloro or bromo,
and the pharmaceutically acceptable acid addition salts thereof, and to processes for their synthesis and intermediates useful in their synthesis. It also relates to the use of the compounds of Formula I, and the pharmaceutically acceptable acid addition salts thereof, as anti-obesity and anti-diabetic agents and to pharmaceutical compositions useful in the treatment of obesity and diabetes.

The preferred compounds of Formula I are those wherein $R_2$ is hydrogen, and the pharmaceutically acceptable acid addition salts thereof, especially the free bases.

Also preferred are the compounds of Formula I wherein $R_1$ is primary or secondary alkyl of 1 to 3 carbon atoms, especially methyl, and the pharmaceutically acceptale acid addition salts thereof, particularly the free bases, as well as the compounds of Formula I wherein R is tertiary alkyl of 4 to 7 carbon atoms, and R' is tertiary alkyl of 4 to 7 carbon atoms, and the pharmaceutically acceptable acid addition salts thereof, particularly the free bases.

More preferred are the compounds of Formula I wherein R is tertiary alkyl of 4 to 6 carbon atoms,
R' is tertiary alkyl of 4 to 6 carbon atom,
$R_1$ is primary or secondary alkyl of 1 to 3 carbon atoms, and
$R_2$ is hydrogen,
and the pharmaceutically acceptable acid addition salts thereof, especially the free bases, and particularly the compounds of this group wherein $R_1$ is primary alkyl of 1 to 3 carbon atoms, and the pharmaceutically acceptale acid addition salts thereof, especially the free bases, and more particularly the compounds of this group wherein $R_1$ is methyl, and the pharmaceutically acceptable acid addition salts thereof, especially the free bases.

In each of the afore-mentioned groups, the compounds wherein R and R' are identical, and the pharmaceutically acceptable acid addition salts thereof, especially the free bases, are most preferred, particularly from the standpoint of ease of synthesis.

The most preferred group of compounds are the compounds of Formula I wherein
R is tertiary alkyl of 4 or 5 carbon atoms,
R' is tertiary alkyl of 4 or 5 carbon atoms with the proviso that R and R' are identical,
$R_1$ is methyl or ethyl, and
$R_2$ is hydrogen,
and the pharmaceutically acceptable acid addition salts thereof, especially the free bases, and more particularly the compounds of the foregoing group wherein
R is t-butyl, and
R' is t-butyl,
and the pharmaceutically acceptable acid addition salts thereof, especially the free bases.

Most preferred is the compound of the formula

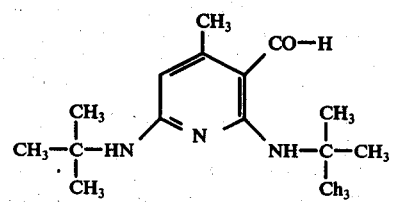

and its pharmaceutically acceptable acid addition salts, especially the free base.

All pharmaceutically acceptable acid addition salts of the compounds of Formula I (i.e., those salts which do not significantly increase the toxicity of the basic compound) are included within the scope of this invention. Included are salts with inorganic acids, e.g., the hydrochloride, hydrobromide, hydroiodide, phosphate (including hydrogen phosphate), metaphosphate, sulfate (including hydrogen sulfate) and perchlorate salts and salts with organic acids, e.g., the acetate, propionate, tartarate, citrate, gluconate, fumarate, malate, maleate, methanesulfonate, ethanesulfonate, benzenesulfonate and p-toluenesulfonate salts. Generally, the hydrochloride, hydrobromide and methanesulfonate salts are the preferred pharmaceutically acceptable acid addition salts. However, the free bases are generally preferred over the pharmaceutically acceptable acid addition salts.

The compounds of Formula I wherein $R_2$ is hydrogen and R and R' are tertiary alkyl of 4 to 7 carbon atoms are synthesized by reacting a ketenimine of the formula

with an amidine of the formula

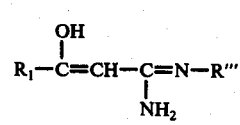

wherein
R" and R'''are tertiary alkyl of 4 to 7 carbon atoms, and
$R_1$ is primary or secondary alkyl of 1 to 5 carbon atoms, in an inert organic solvent at a temperatrue of 15°-60° C., conveniently 20°-30° C., in the presence of a strong base.

As is well known in those in the art, the reaction time necessary is inversely related to the reaction temperature, i.e., the higher the reaction temperature, the shorter the reaction time. It is, therefore, impossible to give a precise reaction time. However, a reaction time of 30–180 minutes is generally acceptable with a reaction time of 30–120 minutes being preferred.

The reaction solvent is not critical. Any inert organic solvent that does not have an acidic hydrogen atom (proton) in which the reactants are soluble, or at least partially soluble, and whose boiling point is at or above the desired reaction temperature and whose freezing point is below the desired reaction temperature may be used. An inert solvent is one that under the reaction conditions employed, does not react with any of the reactants or the desired product and that does not otherwise interfere with the reaction by, for example, reacting with any transitory or long-lived intermediate involved. Among the inert solvents that are suitable are symmetrical and unsymmetrical dialkyl ethets having a total of at least 5 carbon atoms and preferably no more than 10 carbon atoms, cyclic ethers (e.g., p-dioxane and tetrahydrofuran), liquid symmetrical and unsymmetrical 2-lower alkoxyethyl ethers (e.g., bis-2-methoxyethyl ether and bis-2-ethoxyethyl ether) and symmetrical and unsymmetrical dilower alkyl ethers of ethylene glycol (e.g., 1,2-diethoxyethane and 1-ethoxy-2-methoxyethane), and mixtures of these solvents. Tetrahydrofuran and p-dioxane, and mixtures thereof, are particularly suitable. Mixtures of the foregoing solvents with liquid alkanes, e.g., alkanes having 6 to 10 carbon atoms, are also particularly well suited.

The molar ration of the amidine of Formula IV to the ketenimine of Formula III is usually 1:1, however, a small molar excess (e.g., up to 10%) of the ketenimine is occasionally employed.

Any strong base can be employed, for example lithium lower alkyls (e.g., methyl lithium and n-butyl lithium), phenyl lithium, sodium or potassium lower alkoxides (e.g., sodium methoxide and potassium t-butoxide), alkali metal hydroxides (e.g., lithium, sodium and potassium hydroxide), metal hydrides (e.g., sodium hydride and calcium hydride) and lithium di-isopropyl amide. However, non-nucleophilic bases are preferred. The base must be stronger than the amidine employed. Lithium di-isopropyl amide and n-butyl lithium are particularly convenient bases. Generally, one equivalent of base (relative to the amidine) is employed.

The reaction is generally run under an inert atmosphere (e.g., nitrogen, helium, neon, argon, krypton or xenon, or a mixture thereof, preferably nitrogen) by adding a solution of the strong base to the amidine and then adding a solution of the ketenimine to the resulting solution after the initial exothermic reaction has ceased.

Upon conclusion of the reaction, the reaction mixture is worked up by conventional means. If the obtained reaction product is a mixture, it can be separated by conventional techniques, e.g., fractional crystallization and/or gradient elution column chromatography using an adsorbent such as silica and eluents such as mixtures of methanol and chloroform and mixtuures of ethyl acetate and hexane.

The amidines of Formula IV are synthesized by reacting a ketoketenimine of the formula

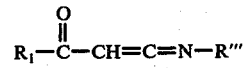

wherein
R''' and $R_1$ are as defined in connection with Formula IV,
with ammonia or by reacting an isoxazolium salt of the formula

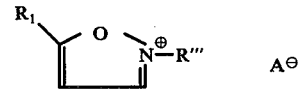

wherein
R''' and $R_1$ are as defined in connection with Formula IV, and
$A^-$ is a non-interfering anion, e.g., perchlorate, tetrafluoroborate, methylsulfate, ethylsulfate, bisulfate, chloride, bromide, iodide or p-toluenesulfonate,
with ammonia. Either reaction is suitably effected by adding a solution of the compound of Formula V or VI in an inert organic solvent, e.g., methylene chloride, to a solution of anhydrous liquid ammonia in an inert organic solvent, preferably the same solvent, i.e., methylene chloride, with stirring at −40° − −60° C. for 5–60 minutes. Although not essential, an inert atmosphere (as defined above) is usually employed. A large molar excess of liquid ammonia to isoxazolium salt or ketoketenimine (e.g., 10–1000 mols) is generally employed.

The ketenimines of Formula III are novel and can be produced by the process set forth below. The ketoketenimines of Formula V are known or can be produced by conventional means as set forth below.

The ketenimines of Formulae III and V are produced from a base such as a tertiary amine (e.g., triethylamine) or sodium carbonate and an isoxazolium salt of the formula

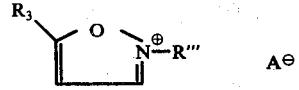

wherein
R''' is tertiary alkyl of 4 to 7 carbon atoms,
$R_3$ is hydrogen or primary or secondary alkyl of 1 to 5 carbon atoms, and
$A^-$ is as defined in connection with Formula VI. See Woodward et al., J. Amer. Chem. Soc. 88, 3,169–3,170 (1966), which is hereby incorporated by reference. The ketenimines are usually stored at or below 0° C. to inhibit decomposition.

The isoxazolium salts of Formulae VI and VII are known or can be produced by a conventional quaternization of the corresponding isoxazoles with a strong alkylating agent, e.g., a dialkyl sulfate or a mixture of a tertiary alkanol, e.g., t-butanol, and perchloric acid. See, for example, Woodward et al., J. Amer. Chem. Soc. 83, 1,007–1,009 (1961), Woodward et al., J. Amer. Chem. Soc. 83, 1,010–1,012 (1961), Woodward et al., J. Amer. Chem. Soc. 88, 3,169–3,170 (1966) and Woodward et al., J. Org. Chem. 31, 2,039–2,040 (1966). The isoxazoles are either known or can be prepared by conventional processes from known precursors.

The compounds of Formula I wherein $R_2$ is hydrogen are peferably synthesized from the corresponding compounds having a cyano group rather than a formyl group in the 3-position, i.e., compounds of the formula

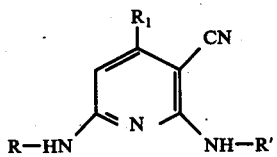

(VIII)

wherein

R, R' and $R_1$ are as defined in connection with Formula I, by reduction with hydrogen, formic acid, Raney nickel and water at a temperature of 8°-40° C., preferably 20°-30° C., most preferably 20°-28° C., with external cooling if necessary. High temperatures should be avoided to preclude cleavage of the R and/or R' groups. The compounds may also be produced using literature reaction conditions, i.e., formic acid, Raney nickel and water at reflux temperature. However, yields are small, particularly where R and/or R' is tertiary alkyl.

Since the Raney nickel is conventionally weighed wet, it is impossible to specify with any degree of precision the amount of Raney nickel required. Likewise, it is impossible to specify the minimum amount of hydrogen, formic acid and water.

However, the reaction is conveniently run by adding 1-10 grams of Raney nickel (wet weight) per gram of compound of Formula VIII to a solution of said compound in an excess of formic acid (conveniently 98-100% formic acid), e.g., 10-50 ml., preferably 15-50 ml., formic acid and ½-5 ml. water per gram of compound of Formula VIII, and bubbling hydrogen slowly through the resulting reaction mixture. It is sometimes necessary to add additional Raney nickel during the course of the reaction, e.g., an additional 1-10 grams (wet weight) per gram of compound of Formula VIII since the Raney nickel catalyst is slowly deactivated. The reaction may also be run in a conventional hydrogenation reactor.

A precise reaction time cannot be given; the reaction is generally run until no more starting material is present. See below. However, a reaction time of 1½-10 hours, preferably 2½-6 hours, is usually acceptable.

the reaction is conveniently monitored by thin layer chromatography using silica gel plates with 30% ethyl acetate/heptane as the solvent. When thin layer chromatography indicates that starting material (compound of Formula VIII) is still present but that it is no longer being converted to the product, additional Raney nickel should be added to the reaction mixture. When, on the other hand, thin layer chromatography indicates that no more starting material is present, the reaction mixture is worked up by conventional means, for example as described in Example 6(b).

This process is particularly useful for the synthesis of the compounds of Formula I
wherein
R is tertiary alkyl of 4 to 7 carbon atoms,
R' is tertiary alkyl of 4 to 7 carbon atoms,
$R_1$ is primary or secondary alkyl of 1 to 5 carbon atoms, and
$R_2$ is hydrogen,
and particularly the compounds of this group wherein
$R_1$ is primary alkyl of 1 to 3 carbons, more preferably methyl or ethyl, nd most preferably methyl,
as well as for the synthesis of the compounds of Formula I
wherein
$R_1$ is primary alkyl of 1 to 3 carbon atoms, more preferably methyl or ethyl and most preferably methyl, and
$R_2$ is hydrogen,
and particularly the compounds of each of these groups wherein
R is tertiary alkyl of 4 to 6 carbon atoms,
R' is tertiary alkyl of 4 to 6 carbon atoms.

The compounds of Formula VIII are disclosed in copending application Ser. No. 533,941, now abandoned, and in the published foreign counterparts thereof, e.g., Belgian patent No. 827,802 and German Offenlegungsschrift 2,514,558. (Also disclosed therein are compounds of Formula I having an alkylcarbonyl, alkoxycarbonyl, optionally substituted benzoyl or carbamoyl group or a hydrogen atom in the 3-position of the pyridine ring. 3-Cyano (and other related) compounds are also disclosed in or embraced by the generic disclosures of Netherlands Application 7,308,294 (or German Offenlegungsschrift 2,230,392 of Belgian Patent No. 801,342 which are equivalents of each other), U.S. Pat. Nos. 3,853,895 and 3,899,478, British Patent Nos. 1,377,505 and 1,377,506, German Offenlegungsschrift 2,211,663 and Bernstein et al., J. Amer. Chem. Soc. 69, 1,151-1,158 (1947).

The compounds of Formula I wherein $R_2$ is chloro or bromo are synthesized from the corresponding compounds wherein $R_2$ is hydrogen by treatment with about one equivalent (e.g., 1-1.02 equivalents) of N-chlorosuccinimide or N-bromosuccinimide in an inert organic solvent, e.g., carbon tetrachloride or a lower alkanol such as ethanol, or a mixture thereof, at a temperature of 0°-30° C., conveniently 20°-25° C., for ½-12 hours, preferably 1-3 hours.

The compounds of Formula I in free base form can be converted into their pharmaceutically acceptable acid addition slats by conventional means. Likewise, any acid addition salt can be converted into the free base by conventional means, e.g., by partition between aqueous 2N. sodium hydroxide and chloroform. Hence, any acid addition salt or free base that is not suitable for pharmaceutical use may be converted by conventional means into a free base or pharmaceutically acceptable acid addition salt that is suitable for such use.

The compounds of Formula I and their pharmaceutically acceptable acid addition salts are useful as anti-obesity and anti-diabetic agents as indicated by (a) glucose transport tests carried out in male Wistar rats and (b) anti-hyperglycemic tests carried out in male ICR mice.

(a) Glucose transport test: Male Wistar rats are dosed orally with 0.3-80 mg./kg. body weight of the test compound after at least 20 hours of fasting. One hour after receiving the drug, each animal is sacrificed and the upper small intestine is removed and washed with glucose-saline. A 5 cm. section of the intestine is everted so that the mucosal surface is on the outside. One end of the segment it tied and the center of the sac so formed is filled with oxygen saturated Kreb's bicarbonate buffer. The other end is then closed to form a sac which is then incubated in 10 ml. of oxygen saturated bicarbonate buffer for 60 minutes at 37° C. Both the outside and inside solutions contain initially 0.3% of glucose. At the end of the incubation time, the glucose content of the outer (mucosal) and the inner (serosal) solution is determined using the standard Auto Analyzer procedure. Similar tests are run simultaneously with control animals receiving only the vehicle. The percent inhibition of glucose transport caused by the drug is calculated from the formula $$I = 100 - \left( \frac{S_t - M_t}{S_c - M_c} \times 100 \right),$$

wherein
I = percent inhibition,
$S_t$ = glucose concentration (mg.%) of serosal fluid at the end of an experiment in the drug-treated animal,
$S_c$ = glucose concentration (mg.%) of serosal fluid at the end of an experiment in the control animal,
$M_t$ = glucose concentration (mg.%) of mucosal fluid at the end of an experiment in the drug-treated animal, and
$M_c$ = glucose concentration (mg.%) of mucosal fluid at the end of an experiment in the control animal.

(b) Anti-hyperglycemic test: 6–8 week old adult male ICR mice having a body weight of 30–35 g. are dosed orally with 50–200 mg./kg. body weight of the test compound after 16 hours of fasting. A control group receiving 0.5% carboxymethyl cellulose vehicle is fun concurrently. One and one-half hours after the mice are dosed with the test compound or the carboxymethyl cellulose vehicle, a glucose challenge of 2 g./kg. body weight p.o. is administered. (See Laboratory Animal Digest 7 (4), 76 (1972).). Twenty-five minutes later, the mice are anesthetized with sodium hexabarbital (85 mg./kg. body weight i.p.). Exactly 30 minutes following administration of the glucose challenge, the blood is collected via cardiac puncture. The blood is placed in an Auto Analyzer cup containing 0.025 cc of a heparin preparation containing 1,000 units/ml. and the samples are capped, shaken and kept in an ice bucket. The glucose content of each sample is measured by the standard Auto Analyzer potassium ferric cyanide method (No. N-2b). To validate the test, a known anti-hyperglycemic standard is included each time the test is run. The activity of the compound is calculated from the formula $$A = \frac{G_c - G_t}{G_c} \times 100,$$

wherein
A = % reduction of the glucose concentration of the blood achieved by the test compound,
$G_c$ = glucose concentration (mg.%) of the blood of the control animals, and
$G_t$ = glucose concentration (mg.%) of the blood of the animals receiving the test compound.

The compounds of Formula I, and the pharmaceutically acceptable acid addition salts thereof, are particularly useful as anti-obesity agents.

The precise dosage of the compound of Formula I, or a pharmaceutically acceptable acid addition salt thereof, to be employed depends upon several factors including the severity of the condition being treated, the mode of administration and the particular compound employed. However, in general, satisfactory results in the treatment of either obesity or diabetes are obtained when a compound of Formula I, or a pharmaceutically acceptable acid addition salt thereof, is administered at a daily dosage of 1–200 mg./kg. body weight p.o. or a dosage of about 75–1500 mg. for most larger mammals. In general, oral administration requires a higher dose than does intravenous administration. Usually, a small dosage is administered initially and the dosage is gradually increased until the optimal dosage for the host under treatment is determined. The daily dosage is usually divided into two to four equal portions. A typical dosage for larger mammals is 25–150 mg. three times a day.

The compounds of Formula I and their phrmaceutically acceptable acid addition salts may be formulated into conventional pharmaceutical compositions and administered by conventional modes of administration.

The compounds may be combined with pharmaceutically acceptable carriers and other conventional pharmaceutical adjuvants and administered orally in the form of tablets, dispersible powders, granules, capsules, elixirs, suspensions and the like or parenterally in the form of an injectable solution or suspension. The compositions may be prepared by conventional means and may contain one or more conventional adjuvants such as sweetening agents (oral compositions only), other flavoring agents (oral compositions only), coloring agents (oral compositions only) and preserving agents.

Tablets may contain the active ingredient in admixture with conventional excipients, i.e., inert diluents such as calcium carbonate, sodium carbonate, lactose, talc and sodium citrate, granulating and disintegrating agents, e.g., starch, gum tragacanth and alginic acid and also certain complex silicates, binding agents, e.g., starch, gelatin and acacia, and lubricating agents, e.g., magnesium stearate, stearic acid, talc and sodium lauryl sulfate. The tablets may be uncoated or coated by known techniques to delay disintegration and absorption in the gastrointestinal tract and thereby provide a sustained action over a longer period.

Capsules may contain a compound of Formula I, or a pharmaceutically acceptable acid addition salt thereof, alone or admixed with an inert solid diluent, e.g., calcium carbonate, calcium phosphate, kaolin, lactose and high molecular weight polyethylene glycols.

Suspensions, syrups and elixirs may contain a compound of Formula I, or a pharmaceutically acceptable acid addition salt thereof, in admixture with any of the conventional excipients utilized for the preparation of such compositions i.e., suspending agents, e.g., methylcellulose, tragacanth and sodium alginate, wetting agents, e.g., lecithin, polyoxyethylene stearate and polyoxyethylene sorbitan monooleate, preservatives, e.g., ethyl p-hydroxybenzoate, and diluents, e.g., ethanol, propylene glycol and glycerin.

Injectable compositions may contain salt and should, if necessary, be buffered to render them isotonic and are sterile.

The preferred pharmaceutical compositions from the stand-point of ease of preparation and administration are solid compositions, particularly tablets and hard-filled capsules.

A typical dosage unit may contain 25 to 1000 mg. of a compound of Formula I, or a pharmaceutically acceptable acid addition salt thereof, more typically 25 to 500 mg.

A representative formulation prepared by conventional techniques for encapsulation in a hard gelatin capsule is:

A. Compound of Formula I, e.g.,
   the compound of Example 6 — 200 mg.
   Lactose (spray-dried) — 160 mg.

| -continued | | |
|---|---|---|
| the compound of Example 6 | 100 | mg. |
| Gum tragacanth | 10 | mg. |
| Lactose (sprayed-dried) | 197.5 | mg. |
| Corn starch | 25 | mg. |
| Talc | 15 | mg. |
| Magnesium stearate | 2.5 | mg. |

As is evident to those in the art, the compounds of Formula I may exist in three principal tautomeric forms, I(a), I(b) and I(c),

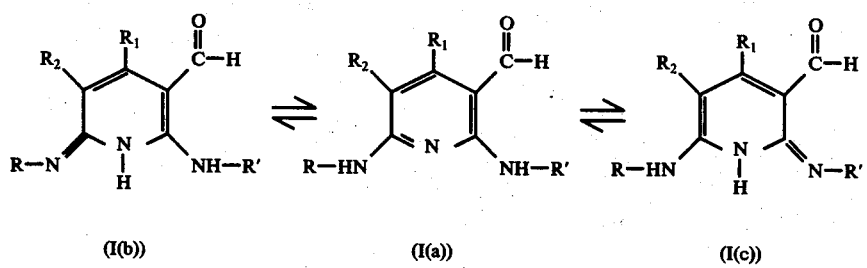

(I(b))   (I(a))   (I(c))

Colloidal silica (Cab-O-Sil) — 6 mg.
Alginic acid — 60 mg.

B. Compound of Formula I, e.g.,
   the compound of Example 6 — 100 mg.
   Powdered lactose — 100 mg.
   Preferably, the active ingredient is micronized by conventional means and then mixed with the diluent.

C. Compound of Formula I, e.g.,
   the compound of Example 6 — 50 mg.
   Powdered lactose — 50 mg.
   Preferably, the active ingredient is micronized by conventional means and then mixed with the diluent.

D. Compound of Formula I, e.g.,
   the compound of Example 6 — 25 mg.
   Powdered lactose — 25 mg.

which rapidly interconvert. For simplicity, Formula I(a) has been used exclusively throughout the specification and claims since it is believed to be the most stable and predominant form. However, it should be understood that Formula I is nothing more than an shorthand notation for Formulae I(a) - I(C) and any other possible tautomeric form. It goes without saying that all other formulae directed to the compounds of Formula I (e.g., Formula II) also embrace the respective tautomeric forms, i.e., the corresponding formulae wherein the hydrogen atoms (protons) and double bonds are as in Formulae I(b) and I(c) and other possible form. Likewise, the compounds of Formula VIII may exist in similar tautomeric forms.

As is also evident to those in the art, the amidines of Formula IV may also exist in tautomeric forms, IV(a) - IV(d)

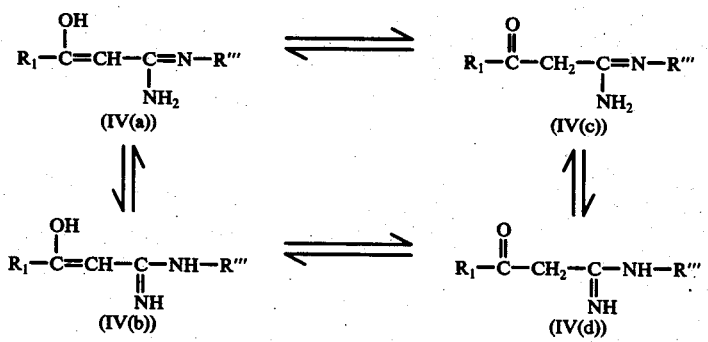

Preferably, the active ingredient is micronized by conventional means and then mixed with the diluent.
A typical tablet may contain:

| D. Compound of Formula I, e.g., | | |
|---|---|---|
| the compound of Example 6 | 25 mg. | |
| Powdered lactose | 25 mg. | |
| Preferably, the active ingredient is micronized by conventional means and then mixed with the diluent. | | |

Compound of Formula I, e.g., the wherein the carbon-carbon double bonds are cis or trans, i.e., the -OH and -H groups are cis or trans to each other, and hydrogen bonded forms thereof, all of which interconvert. For simplicity, Formula IV(a) has been used exclusively throughout the specification. However, it should be understood that Formula IV is nothing more than a shorthand notation for Formulae IV(a) - IV(d). It likewise goes without saying that Formula X embraces the corresponding tautomeric forms, i.e., the formulae wherein the protons and II bonds are as in Formulae IV(b) - IV(d).

The following examples show representative compounds encompassed by this invention and their synthe-

EXAMPLE 1

2-t-Butyl-5-methylisoxazolium perchlorate

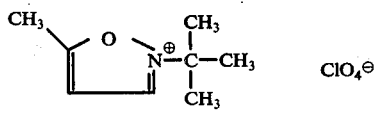
(IX)

1 kg. of 5-methylisoxazole and 892 g. of t-butanol were stirred under nitrogen at 0° C. and 6.37 kg. of 60% perchloric acid were slowly added over a 2½ hour period with vigorous stirring at 0°-5° C. The resulting suspension was allowed to warm to room temperature and stirred overnight. The reaction mixture was then slowly added to a mixture of 20 l. of tetrahydrofuran and 10 l. of ether at 0°-10° C. over a 2 hr. period with stirring. The mixture was then cooled to −5° C. and stirred for an additional 2 hrs. The product (1.821 kg.) was washed well with ether, m.p. 120°-122° C. A second crop (171 g.) was obtained from the mother liquor, m.p. 118°-121° C.

EXAMPLE 2

N'-t-Butyl-3-hydroxybutenamidine

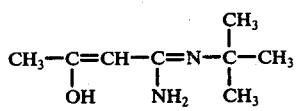
(X)

A solution of 900 g. of 2-t-butyl-5-methylisoxazolium perchlorate in 1.80 l. of methylene chloride dried over aluminum oxide was added with stirring to a mixture of 900 ml. of freshly distilled ammonia and 900 ml. of methylene chloride dried over aluminum oxide at −50° - −60° C. with stirring. The reaction mixture was allowed to come to room temperature and was stirred overnight, and the trapped excess ammonia was stripped off at aspirator pressure at 20°-25° C. for 1 hr. The precipitated solids were removed by filtration and washed with methylene chloride. The combined filtrate and washings were washed twice with 2 l. portions of saturated potassium carbonate solution, dried well over anhydrous sodium sulfate and filtered. Removal of the methylene chloride at reduced pressure and a temperature of about 45° C. gave a solid. Crystallization from ethyl acetate and washing with ethyl acetate/ether gave the product (437 g.), m.p. 126°-129° C. A second crop (59 g.) was also obtained, m.p. 119°-125° C.

EXAMPLE 3

4-t-Butylimino-3-buten-2-one

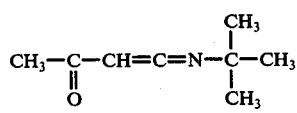
(XI)

To a mixture of 700 ml. of triethylamine and 1.50 l. of methylene chloride dried over aluminum oxide cooled to −10° - −5° C., 1.0 kg. of 2-t-butyl-5-methylisoxazolium perchlorate was added portionwise over a 2½ hr. period, so as to maintain the temperature of the reaction mixture at −5°-0° C., with vigorous stirring. Upon completion of the addition, the reaction mixture was stirred for an additional 1 hr. at −5° - 0° C. The reaction mixture was then poured over 38 l. of carbon tetrachloride at room temperature with vigorous stirring; oily solids separated. 15 lbs. of anhydrous sodium sulfate were added and the reaction mixture was stirred for 30 minutes. The suspension was filtered and the solids were washed with carbon tetrachloride. The combined filtrate-washings were concentrated at about 50° C. and reduced pressure to obtain a dark orange-yellow oil. Distillation at high vacuum yielded the product (522 g.), b.p. 54°-55° C. (0.8 mm Hg.).

EXAMPLE 4

2-t-Butylisoxazolium perchlorate

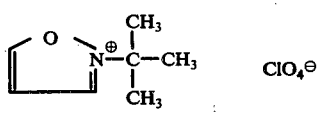
(XII)

To a solution of 24.6 g. (0.356 mol) of isoxazole in 27 g. of t-butanol and 2 ml. of tetrahydrofuran cooled to −10° C. and stirred under nitrogen, 95 ml. of 70% perchloric acid were added dropwise. The resulting solution was allowed to warm to room temperature and was stirred overnight. The yellowish-tan solution was poured into a mixture of 600 ml. of tetrahydrofuran and 600 ml. of ether whereupon white crystals separated. The obtained crystals (72.4 g.) were filtered and washed with ether, m.p. 163°-164° C. (decomp.; began to darken at 152° C.). A second crop (3.36 g.) was obtained from the chilled filtrate, m.p. 160°-162° C.

EXAMPLE 5

3-t-Butylimino-2-propen-1-one

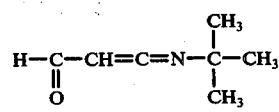
(XIII)

A suspension of 4.51 g. (20 mmol.) of 2-t-butylisoxazolium perchlorate (Compound XII) in 30 ml. of methylene chloride was chilled by addition of ice. To the resulting reaction mixture, 30 ml. of 2N. sodium carbonate and additional ice were added. The reaction mixture was well stirred for 5-10 minutes whereupon it separated into an orange-yellow organic phase and a colorless aqueous phase. The organic (methylene chloride) phase was separated and the aqueous phase was re-extracted twice with methylene chloride. The three methylene chloride extracts were combined, dried over anhydrous sodium sulfate and anhydrous magnesium sulfate and evaporated at reduced pressure to obtain the crude product as a red oil (1.87 g.).

EXAMPLE 6

2,6-Di-t-butylamino-3-formyl-4-methylpyridine (II)

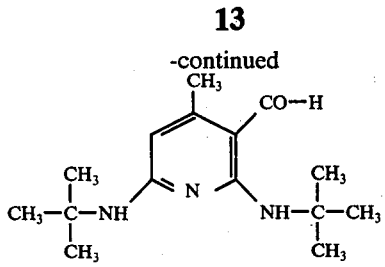

a. A suspension of 1.60 g. (10.2 mmol) of N'-t-butyl-3-hydroxybutenamidine (Compound X) in 11 ml. of dry tetrahydrofuran was stirred under nitrogen. To the suspension, 6.3 ml. of a 1.62 M. solution of n-butyl lithium in hexane (10.2 mmol) were added slowly during which the temperature was maintained at 25°–30° C. with an ice-water bath. Stirring was continued for 45 minutes. To the stirred solution, a solution of 1.28 g. (10.2 mmol.) of 3-t-butylimino-2-propen-1-one (Compound XIII) in 5 ml. of dry tetrahydrofuran was added at 20°–25° C., with external cooling, followed by two dry tetrahydrofuran rinses of the equipment. Stirring was continued for an additional 1½ hrs. The reaction mixture was then poured into a mixture of 5 g. of ammonium chloride and 100 ml. of ice water and water and methylene chloride rinses of the reaction flask were added. The resulting mixture was extracted three times with methylene chloride and the methylene chloride extracts were combined, dried over anhydrous sodium sulfate and anhydrous magnesium sulfate and evaporated at reduced pressure to obtain a red foam (2.4 g.). The foam was dissolved in methanol and a small amount of insoluble material was removed by filtration. Since addition of water to the filtrate resulted in formation of an oil, it was revaporated to a foam at reduced pressure. The next day the oil was dissolved in chloroform; hexane was slowly added to the resulting solution until it became cloudy. The solution was put on a silica column (10 ml.; 1 × 11½ cm.) and eluted with 50% chloroform/hexane. The first two 20 ml. fractions contained virtually all of the two major products. The two fractions were evaporated to oils, both of which were very soluble in heptane. The oils were combined, applied in 100% hexane to 125 ml. of silica (28 mm. column diameter) and eluted with 10% ethyl acetate/hexane. Four fractions were obtained. The fourth fraction, after evaporation of the eluant at reduced pressure, was triturated with heptane to give the desired product (0.05 g.), m.p. 145° – 146° C. The mother liquor from he trituration and the third chromatography fraction were combined and purified on a silica preparatory chromatography plate using three runs with 5% ethyl acetate in hexane. The desired material was removed from the plate and recrystallized from heptane to obtain additional product (0.05 g.), m.p. 141°–143° C.

NMR (CDCl$_3$):
1.48 δ (9 proton singlet)
1.52 δ (9 proton singlet)
2.27 δ (3 proton singlet)
4.77 δ (1 proton broad band)
5.43 δ (1 proton broadened singlet)
9.77 δ (2 proton singlet)

IR (CHCl$_3$): 3460, 2990, 2950, 2890, 1570-1630, 1500-1350, 1450, 1415, 1390, 1360, 1330, 1297, 1190-1260, 1150, 1096, 1026, 950, 920, 900, 830, 660-800, 630, 596, 564, cm.$^{-1}$.

ED$_{50}$ (Test (a)): 0.5 mg/kg.

b. 1.36 g. (5.2 mmol) of 2,6-di-t-butylamino-3-cyano-4-methylpyridine were dissolved in 30 ml. of 98–100% formic acid and 0.5 ml. water and 3.0 g. (wet weight) of Raney nickel were added. Hydrogen was then slowly bubbled through the reaction mixture as it was stirred at room temperature (22°–26° C.) for 2 hrs. (Thin layer chromatography (silica gel plate using 30% ethyl acetate/heptane) showed approximately 50–60% conversion to product.) An additional 3.0 g. (wet weight) of Raney nickel were added and hydrogen was bubbled through the reaction mixture for an additional 3 hrs. as it was stirred at room temperature. (Thin layer chromatography indicated the absence of starting material.) The Raney nickel catalyst was removed by filtration and washed with tetrahydrofuran. The tetrahydrofuran washing was combined with the filtrate and an equal volume of ether was added thereto to precipitate the nickel salts. The nickel salts were removed by filtration and the filtrate was evaporated to dryness at reduced pressure. The residue was dissolved in a minimum amount of a mixture of ethyl acetate and heptane (approximately 30% of the former) and placed on 50 ml. silica gel (column diameter 2.5 cm.) and the product was eluted with 10% ethyl acetate/heptane. Evaporation of the solvent at reduced pressure yielded the product (1.0 g.), m.p. 142.5°–145° C. Recrystallization from heptane yielded the pure product, m.p. 145°–146° C.

EXAMPLE 7

5-Bromo-2,6-di-t-butylamino-3-formyl-4-methylpyridine

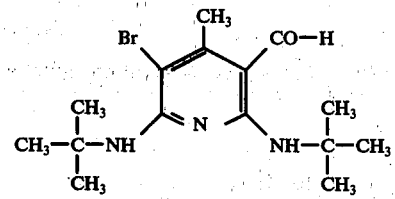

The product is obtained by adding 53.4 mg. (0.3 mmol) of N-bromosuccinimide (recrystallized from water) in small portions to a solution of 78.9 mg. (0.3 mmol) of 2,6-di-t-butylamino-3-formyl-4-methylpyridine (Compound II) in 5 ml. of carbon tetrachloride and 2½ ml. of ethanol, allowing the reaction mixture to stand overnight at room temperature, evaporating the reaction mixture at reduced pressure, partitioning the residue between ether and water, drying the organic phase over anhydrous sodium sulfate and anhydrous magnesium sulfate and removing the ether at reduced pressure.

EXAMPLES 8–15

Other compounds of Formula I that are synthesized by the process of the foregoing examples are:

Example 8: 5-chloro-2,6-di-t-butylamino-3-formyl-4-methylpyridine
Example 9: 2,6-di-t-amylamino-3-formyl-4-methylpyridine
Example 10: 2-t-amylamino-6-t-butylamino-3-formyl-4-methylpyridine
Example 11: 2,6-di-t-butylamino-3-formyl-4-isopropylpyridine
Example 12: 2,6-di-(1,1-diethylpropylamino)-3-formyl-4-methylpyridine Example 13: 2,6-di-t-butylamino-4-ethyl-3-formylpyridine Example 14: 2,6-di-isopropylamino-4-methyl-3-formylpyridine Example 15: 2,6-di-sec-butylamino-4-methyl-3-formylpyridine.

The N.M.R. spectrum was taken at ambient temperature on a 60 MHz N.M.R. spectrometer and the chemical shifts are given in p.p.m. (δ) relative to tetramethylsilane. For anything other than a singlet, the indicated δ value is the mid-point of the peak.

What is claimed is:

1. A compound of the formula

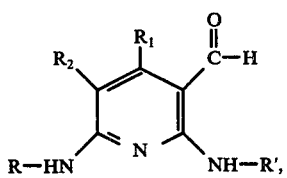

wherein
R is secondary alkyl of 3 to 7 carbon atoms or tertiary alkyl of 4 to 7 carbon atoms,
R' is secondary alkyl of 3 to 7 carbon atoms or tertiary alkyl of 4 to 7 carbon atoms,
$R_1$ is primary or secondary alkyl of 1 to 5 carbon atoms, and
$R_2$ is hydrogen, chloro or bromo,
or a pharmaceutically acceptable acid addition salt thereof.

2. A compound according to claim 1 wherein $R_2$ is hydrogen, or a pharmaceutically acceptable acid addition salt thereof.

3. A compound according to claim 2
wherein
R is tertiary alkyl of 4 to 6 carbon atoms,
R' is tertiary alkyl of 4 to 6 carbon atoms, and
$R_1$ is primary or secondary alkyl of 1 to 3 carbon atoms,
or a pharmaceutically acceptable acid addition salt thereof.

4. A compound according to claim 3
wherein
R is tertiary alkyl of 4 or 5 carbon atoms,
R' is tertiary alkyl of 4 or 5 carbon atoms, with the proviso that R and R' are identical, and
$R_1$ is methyl or ethyl,
or a pharmaceutically acceptable acid addition salt thereof.

5. The compound according to claim 4 having the formula

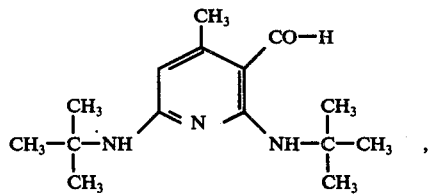

or a pharmaceutically acceptable acid addition salt thereof.

6. The compound according to claim 5 having the formula

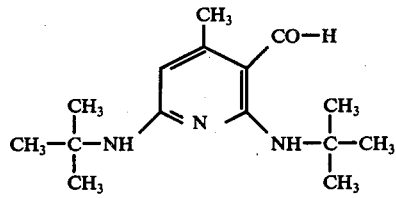

7. A pharmaceutical composition comprising an effective amount of a compound according to claim 1, or a pharmaceutically acceptable acid addition salt thereof, and a pharmaceutically acceptable carrier, said amount being an amount effective for the treatment of obesity or diabetes.

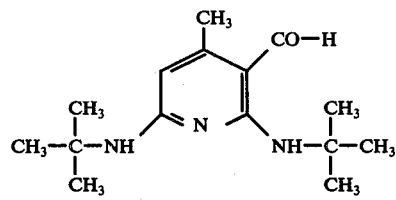

8. A pharmaceutical composition according to claim 7, said composition being a solid or a sterile liquid.

9. A pharmaceutical composition according to claim 7 comprising the compound of the formula

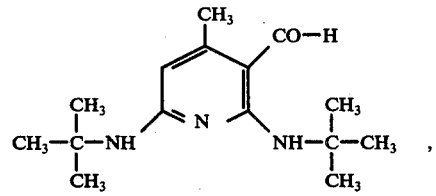

or a pharmaceutically acceptable acid addition salt thereof.

10. A pharmaceutical composition according to claim 9 comprising the compound of the formula

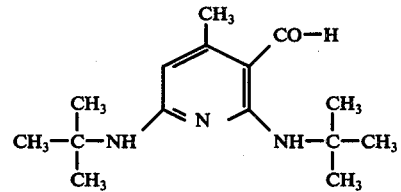

11. A pharmaceutical composition according to claim 10 in unit dosage form.

12. A pharmaceutical composition comprising an effective amount of a compound according to claim 1, or a pharmaceutically acceptable acid addition salt thereof, and a pharmaceutically acceptable carrier, said amount being an amount effective for the treatment of obesity.

13. A method of treating obesity comprising administering to an obese host an effective amount of a compound according to claim 1, or a pharmaceutically acceptable acid addition salt thereof.

14. A method of treating obesity according to claim 13 wherein the compound is the compound of the formula

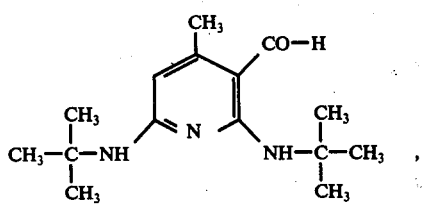

or a pharmaceutically acceptable acid addition salt thereof.

15. A method of treating obesity according to claim 14 wherein the compound is the compound of the formula

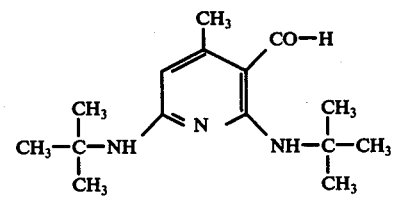

16. A method of treating diabetes comprising administering to a diabetic host an effective amount of a compound according to claim 1, or a pharmaceutically acceptable acid addition salt thereof.

17. A method of treating diabetes according to claim 16 wherein the compound is the compound of the formula

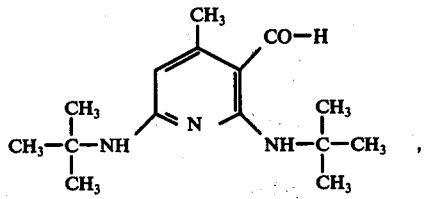

or a pharmaceutically acceptable acid addition salt thereof.

18. A method of treating diabetes according to claim 17 wherein the compound is the compound of the formula

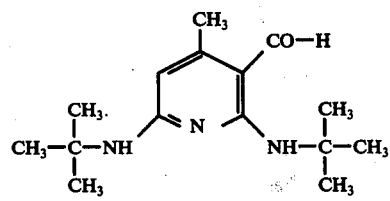

* * * * *